(12) United States Patent
Dwyer et al.

(10) Patent No.: US 11,471,636 B2
(45) Date of Patent: Oct. 18, 2022

(54) MOISTURE REMOVAL AND CONDENSATION AND HUMIDITY MANAGEMENT APPARATUS FOR A BREATHING CIRCUIT

(71) Applicant: Medline Industries, LP, Springfield, IL (US)

(72) Inventors: Daniel Patrick Dwyer, Cary, NC (US); James Lorek, Cary, NC (US)

(73) Assignee: Medline Industries, LP, Springfield, IL (US)

( * ) Notice: Subject to any disclaimer, the term of this patent is extended or adjusted under 35 U.S.C. 154(b) by 448 days.

(21) Appl. No.: 15/099,051

(22) Filed: Apr. 14, 2016

(65) Prior Publication Data

US 2016/0303342 A1    Oct. 20, 2016

Related U.S. Application Data

(60) Provisional application No. 62/148,077, filed on Apr. 15, 2015.

(51) Int. Cl.
*A61M 16/08* (2006.01)
*A61M 16/16* (2006.01)

(52) U.S. Cl.
CPC .... *A61M 16/0808* (2013.01); *A61M 16/0875* (2013.01); *A61M 16/16* (2013.01);
(Continued)

(58) Field of Classification Search
CPC .............. A61M 16/08; A61M 16/0808; A61M 16/0875; A61M 16/16; A61M 16/162;
(Continued)

(56) References Cited

U.S. PATENT DOCUMENTS 2,702,089 A  2/1955  Engelder
3,747,598 A  7/1973  Cowans
(Continued)

FOREIGN PATENT DOCUMENTS

EP  0533644 A2  3/1993
EP  0794809 A1  9/1997
(Continued)

OTHER PUBLICATIONS

"Technical Note TN-157: Moisture Exchange Tubes for Humidity Control of Test Gases," Raesystems by Honeywell, Jul. 29, 2014.

*Primary Examiner* — LaToya M Louis
(74) *Attorney, Agent, or Firm* — Quarles & Brady LLP

(57) ABSTRACT

A moisture removal and condensation and humidity management apparatus for a breathing circuit includes a breathing circuit tubing defining a breathing gas conduit. The breathing gas has a first humidity level and a level of moisture therein. A dry gas conduit is adjacent at least a portion of the breathing gas conduit. The dry gas flow is configured to have a second humidity level lower than the first humidity level. A moisture transmission pathway is provided between the breathing gas conduit and the dry gas conduit, such that humidity in the flow of breathing gas is lowered and moisture is transferred to the dry gas flow. The moisture transmission pathway may be provided by a permeable portion which is permeable to water vapor but impermeable to liquid water, or by one or more perforations which permit drainage of liquid water from the breathing gas conduit to the dry gas conduit.

10 Claims, 2 Drawing Sheets

(52) U.S. Cl.
CPC ..... *A61M 16/0816* (2013.01); *A61M 2205/33* (2013.01); *A61M 2205/75* (2013.01); *A61M 2205/7536* (2013.01)

(58) Field of Classification Search
CPC ... A61M 16/14; A61M 16/142; A61M 16/145
See application file for complete search history.

(56) References Cited

U.S. PATENT DOCUMENTS

| | | | |
|---|---|---|---|
| 4,146,597 A | | 3/1979 | Eckstein et al. |
| 4,155,961 A | * | 5/1979 | Benthin ................ A61M 16/16 |
| | | | 128/204.13 |
| 4,200,094 A | | 4/1980 | Gedeon et al. |
| 4,232,667 A | | 11/1980 | Chalon et al. |
| 4,318,398 A | | 3/1982 | Oetjen et al. |
| 4,355,636 A | | 10/1982 | Oetjen et al. |
| 4,381,267 A | | 4/1983 | Jackson |
| 4,637,384 A | | 1/1987 | Schroeder |
| 4,808,201 A | | 2/1989 | Kertzman |
| 4,897,359 A | | 1/1990 | Oakley et al. |
| 5,042,500 A | | 8/1991 | Norlien et al. |
| 5,062,145 A | * | 10/1991 | Zwaan ................ A61M 16/16 |
| | | | 392/395 |
| 5,501,212 A | | 3/1996 | Psaros |
| 6,213,120 B1 | | 4/2001 | Block et al. |
| 6,220,245 B1 | | 4/2001 | Takabayashi et al. |
| 6,523,538 B1 | | 2/2003 | Wikefeldt |
| 6,662,802 B2 | | 12/2003 | Smith et al. |
| 6,769,431 B2 | | 8/2004 | Smith et al. |
| 6,953,354 B2 | | 10/2005 | Edirisuriya et al. |
| 7,097,690 B2 | | 8/2006 | Usher et al. |
| 7,588,029 B2 | | 9/2009 | Smith et al. |
| 7,802,569 B2 | * | 9/2010 | Yeates ................ A61M 15/0086 |
| | | | 128/203.12 |
| 8,037,882 B2 | | 10/2011 | Smith et al. |
| 8,105,410 B2 | | 1/2012 | Roth et al. |
| 8,236,081 B2 | | 8/2012 | Roth et al. |
| 8,453,641 B2 | | 6/2013 | Payton et al. |
| 8,616,202 B2 | | 12/2013 | Tatkov et al. |
| 9,067,036 B2 | | 6/2015 | Korneff et al. |
| 9,827,393 B2 | | 11/2017 | Smith et al. |
| 2007/0157929 A1 | | 7/2007 | Radomski et al. |
| 2007/0157931 A1 | * | 7/2007 | Parker ................ A61M 11/005 |
| | | | 128/204.23 |
| 2008/0110458 A1 | * | 5/2008 | Srinivasan ........... A61M 11/041 |
| | | | 128/203.26 |
| 2008/0229605 A1 | | 9/2008 | Brown |
| 2009/0088656 A1 | | 4/2009 | Levitsky et al. |
| 2013/0098360 A1 | * | 4/2013 | Hurmez ................ A61M 13/003 |
| | | | 128/203.12 |
| 2013/0112201 A1 | | 5/2013 | Graham et al. |
| 2013/0303977 A1 | | 11/2013 | Spearman et al. |
| 2014/0261416 A1 | | 9/2014 | Arcilia et al. |
| 2015/0048530 A1 | | 2/2015 | Cheung et al. |
| 2016/0045702 A1 | | 2/2016 | Milne et al. |

FOREIGN PATENT DOCUMENTS

| | | |
|---|---|---|
| EP | 2283888 A1 | 2/2011 |
| EP | 2335760 A1 | 6/2011 |
| GB | 1 431 558 A | 4/1976 |
| GB | 2139110 A | 11/1984 |
| JP | 2000024111 A | 1/2000 |

\* cited by examiner

MOISTURE REMOVAL AND CONDENSATION AND HUMIDITY MANAGEMENT APPARATUS FOR A BREATHING CIRCUIT

CROSS REFERENCE TO RELATED APPLICATION

This application claims the benefit of U.S. provisional application 62/148,077, filed Apr. 15, 2015, the disclosure of which is hereby incorporated by reference in its entirety.

FIELD OF THE INVENTION

The present invention relates generally to a medical device. More particularly, the present invention is related to a moisture removal and condensation and humidity management apparatus for placement with a breathing circuit.

BACKGROUND

A breathing circuit delivers medical gas to a patient under pressure in a prescribed volume and breathing rate. The medical gas is often humidified by a humidifier located at or near the ventilator or respirator. The optimum respiratory circuit delivers 100% RH medical gases to the patient while reducing the amount of humidity and subsequent condensate delivered back to the ventilator through the expiratory limb. Therefore, the humidified gas has to travel through all or most of the tubing and has time to cool. Cooling of the gas leads to rainout or condensation in the breathing tube and collection of water within the breathing circuit.

Several possible solutions to the problem of rainout have been developed. One such proposed solution is a heating wire provided along the length of the tube. The wire may be provided within the interior of the tubing or alternatively may be embedded along the interior of the tubing. The wire heats the humidified gas traveling through the tubing to prevent the gas from cooling, thus preventing the problem of water condensing out of the gas traveling through the breathing circuit. However, the manufacture of such heated wire respiratory circuits can be time consuming and costly.

Another possible solution, which eliminates the heated wire, is to provide a water collection device somewhere within the breathing circuit. A water collection apparatus is typically placed in the expiratory limb of the respiratory circuit to collect and allow for manual removal of excessive condensation prior to the gases entering the ventilator or respirator. It is known that excessive condensate entering a ventilator or respirator from the expiratory limb of a respiratory circuit can harm the device.

Most frequently, the water collection device is designed to trap the condensed water vapor in a removable container. When the container is removed, a valve can be actuated to create a gas tight seal for the breathing circuit. However, this type of water collection device has to be monitored and manually emptied, causing risk of patient or caregiver infection. The removal of moisture and condensation management is not automatic. Furthermore, the removable container is often only at one discrete point along the breathing circuit, and may need to be lowered to gravitationally collect liquid, which may be impractical.

Another possible solution is to provide a permeable membrane in the breathing circuit tubing which is permeable to water vapor but impermeable to liquid water, such that moisture inside the breathing gas flow inside such tubing dissipates to outside the tubing via such a membrane, and out to the ambient air surrounding the tubing. The problem with this solution is at least two-fold: first, such a thin walled membrane which is exposed to the surroundings can be easily punctured or damaged; and second, due to a relatively high humidity in the ambient conditions, there can be a limited humidity differential between the breathing gas flow and the ambient surroundings, so that the capacity for moisture to dissipate passively through the permeable membrane to ambient surroundings can also be limited.

Accordingly, it is desirable to provide an improved apparatus for removing or decreasing water vapor, moisture, or condensate in a breathing circuit. It is further desirable that the improved apparatus for removing water vapor, moisture or condensate from the breathing tube, eliminates the need to monitor the device or to heat the exhalation limb of the breathing tube, and is not dependent on the positioning of the device, protects the device and its moisture and humidity transmission mechanism from damage, and increases its capacity for moisture removal and condensation management in a breathing circuit.

SUMMARY OF THE INVENTION

The foregoing needs are met, to a great extent, by the present invention, wherein a moisture removal and condensation and humidity management apparatus for a breathing circuit arranged between a patient and a ventilator is provided, comprising a breathing circuit tubing defining a breathing gas conduit for a flow of breathing gas therein, the breathing gas having a first humidity level and a level of moisture or condensate therein. A dry gas conduit is disposed adjacent at least a portion of the breathing gas conduit for a dry gas flow in said dry gas conduit, the dry gas flow being configured to have a second humidity level lower than the first humidity level. A moisture transmission pathway is included between the breathing gas conduit and the dry gas conduit, such that humidity in the flow of breathing gas is lowered and moisture or condensate in the flow of breathing gas is transferred to the dry gas flow. The dry gas conduit is closed to ambient air around the apparatus In one embodiment of the present invention, the breathing circuit tubing comprises a permeable portion which is permeable to water vapor but impermeable to liquid water, such that the moisture transmission pathway is provided by such permeable portion of the breathing circuit tubing.

In another embodiment of the present invention, the breathing circuit tubing is formed by an inner tube defining the breathing gas conduit, and the dry gas conduit is formed by an outer tube surrounding the inner tube, the dry gas conduit being defined by an annular flow conduit defined between the inner tube and outer tube.

In another embodiment of the present invention, the breathing circuit tubing is formed by an inner tube defining the breathing gas conduit, and the dry gas conduit is formed by an outer tube surrounding the inner tube, an annular space being defined between the inner tube and outer tube. Furthermore, a dividing wall is formed between the inner tube and outer tube in the annular space to divide the dry gas conduit into a first, delivery conduit for flow of dry gas from a first end of the apparatus to a second end of the apparatus, and a second, return conduit for flow of dry gas from the second end of the apparatus to the first end of the apparatus.

In another embodiment of the present invention, the permeable portion of the breathing circuit tubing is a permeable membrane which forms a portion of said breathing circuit tubing.

In another embodiment of the present invention, the breathing circuit tubing comprises one or more perforations which permit drainage of liquid water from the breathing gas conduit to the dry gas conduit, such that the moisture transmission pathway is provided by such one or more perforations of the breathing circuit tubing.

In another embodiment of the present invention, the breathing circuit conduit and dry gas conduit share a common dividing wall, the common dividing wall having the moisture transmission pathway.

In another embodiment of the present invention, the common dividing wall comprises a permeable portion which is permeable to water vapor but impermeable to liquid water, such that the moisture transmission pathway is provided by such permeable portion of the common dividing wall.

In another embodiment of the present invention, the permeable portion of the breathing circuit tubing is a permeable membrane which forms a portion of said common dividing wall.

In another embodiment of the present invention, the common dividing wall comprises one or more perforations which permit drainage of liquid water from the breathing gas conduit to the dry gas conduit, such that the moisture transmission pathway is provided by such one or more perforations of the common dividing wall.

In another embodiment of the present invention, an exit port is provided on the apparatus for the dry gas conduit having a filter, the dry gas exiting via the exit port to the ambient environment surrounding the apparatus.

In another embodiment of the present invention, an input port is provided on the apparatus for the dry gas conduit having a flow or volumetric control element for the dry gas flow.

In another embodiment of the present invention, an exit port is provided on the apparatus for the dry gas conduit which is connected to a source of suction.

In another aspect of the present invention, method of removing moisture or controlling condensation in a breathing circuit is provided, comprising providing an apparatus as disclosed in any of the preceding recited embodiments of the present invention. The apparatus is configured and arranged to be disposed between a ventilator and a patient. Breathing gas is supplied via the breathing circuit tubing to a patient. And dry air is supplied through the dry gas conduit to remove moisture or liquid water condensate from the breathing gas conduit. In another embodiment, one or more of the first and second humidity levels may be monitored using a humidity sensor. In one or more further embodiments, the breathing circuit tubing is an expiratory limb of a ventilator circuit.

There has thus been outlined, rather broadly, certain embodiments of the invention in order that the detailed description thereof herein may be better understood, and in order that the present contribution to the art may be better appreciated. There are additional embodiments of the invention that will be described below and which form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of embodiments in addition to those described and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

DETAILED DESCRIPTION

Figure 1:
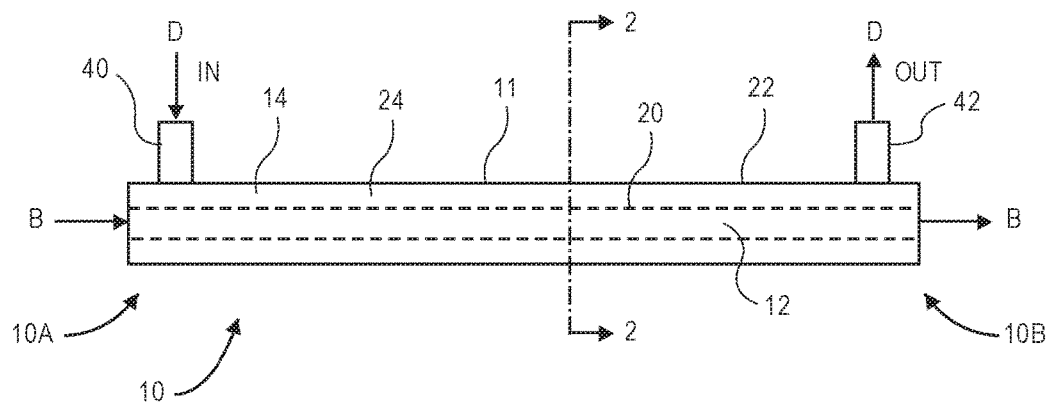
FIG. 1 is a schematic view illustrating an apparatus incorporated into or as part of a breathing gas circuit in accordance with one or more embodiments of the present invention.

The invention will now be described with reference to the drawing figures, in which like parts are referred to with like reference numerals throughout. One or more embodiments in accordance with the present invention provide a moisture removal and condensation and humidity management apparatus for a breathing circuit to rapidly remove water vapor or condensate from a humidified medical gas traveling through a breathing circuit between a ventilator and a patient or the patient and the ventilator. As used herein, a "breathing circuit" or "breathing gas circuit" is any arrangement of tubing or conduits which carries gases to be administered to and from a patient, such as from a ventilator, and which may include additional accessories or devices attached to it. Such "breathing gases" may include oxygen, air or any component thereof, and are configured for absorbing high levels of moisture and/or being humidified prior to administration to a patient, or during administration to a patient, suitable for medical applications.

FIG. 1 is a schematic view illustrating an apparatus incorporated into or as part of a breathing gas circuit in accordance with one or more embodiments of the present invention. A moisture removal and condensation and humidity management apparatus 10 for a breathing circuit includes a section or length of breathing circuit tubing 11 defining a breathing gas conduit 12 for a flow (B) of breathing gas therein. The breathing gas flows from a first, upstream end 10A of the device 10, through the conduit 12 defined within device 10, to a second, downstream end 10B of the device 10. The breathing gas is configured to have a first humidity level and a level of moisture therein, which may be calibrated based on the needs of the patient. In one embodiment such a length of breathing circuit tubing 11 may be in an expiratory limb of a breathing circuit, such as, for example, somewhere between a patient and a ventilator. In the device 10, a dry gas conduit 14 is defined adjacent at least a portion of the breathing gas conduit 12 between the first end 10A and second end 10B, for a dry gas flow (D) therein. The dry gas flow (D) is configured to have a second humidity level which is lower than the first humidity level within the breathing gas conduit (B). A dry gas flow is coupled from a dry gas source (not shown) to one or more input ports 40 which feed the dry gas flow (D) into the dry gas conduit 14, which then flows substantially parallel to, or around the breathing gas conduit 12.

Figure 2:
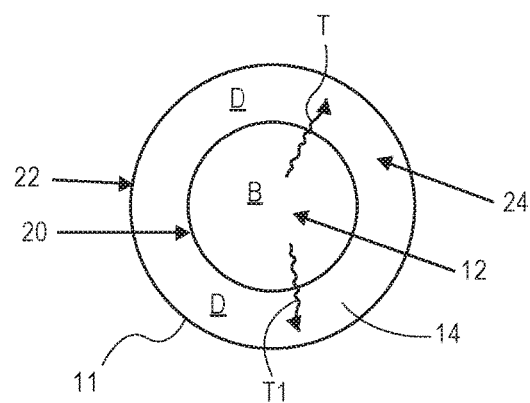
FIG. 2 a schematic cross-sectional view illustrating the apparatus of FIG. 1 in one or more embodiments of the present invention.

FIG. 2 a schematic cross-sectional view illustrating the apparatus of FIG. 1 in one or more embodiments of the present invention. As shown in FIG. 2, the dry gas conduit 14 may be an annular flow space which is concentric with breathing gas conduit 12. In the embodiment shown in FIG. 2, the breathing circuit tubing 11 may be formed by an inner tube 20 defining the breathing gas conduit 12, and the dry gas conduit 14 is formed by an outer sleeve or tube 22 surrounding the inner tube 20, the dry gas conduit 14 thereby being defined as an annular flow conduit 24 defined between the inner tube 20 and outer tube 22. One, or both, of the inner and outer conduits may be formed by corrugated tubing. Alternatively, the inner tube 20 could define the dry gas conduit 14 and the annular space 24 between the inner and outer tubes 20, 22 could be the breathing gas conduit 12. In the present invention, a sufficient stretch of surface area is shared along the breathing circuit tubing 11 between the breathing gas conduit 12 and dry gas conduit 14 such that a moisture and humidity transmission pathway is enabled between the two conduits, as further described below.

The present invention provides one or more embodiments which provide a moisture transmission pathway between the breathing gas conduit 12 and the dry gas conduit 14, such that humidity in the flow of breathing gas (B) is lowered and moisture in the flow of breathing gas (B) is transferred to the dry gas flow (D). In FIG. 2, such a moisture transmission pathway (T) occurs between the higher humidity breathing gases in conduit 12 and the lower humidity dry gas flow in conduit 14. A user can increase or decrease the level of dry gas supplied to the circuit to manage or remove the condensate which may be transmitted from the breathing gas (B) to the dry gas conduit. The moisture level thus may be reduced from within the breathing gas flow and transferred to the dry gas flow. In one or more embodiments, such as shown in FIG. 2, the breathing circuit tubing 11 comprises a permeable portion (not shown) along part or all of the inner conduit 20 is provided, which is permeable to water vapor but impermeable to liquid water, such that the moisture transmission pathway (T) is provided by such permeable portion of the breathing circuit tubing. The materials comprising the permeable portion are water vapor breathable and allow passage of water vapor, as is well known to those of ordinary skill in the art. The permeable portion may form some or all of the walls of the breathing gas conduit 12, such as inner tube 20, and may include a single, or composite outer, layer of water vapor breathable medium. In one embodiment, an additional wicking layer may be added to the permeable portion. In the embodiment shown in FIG. 2, the additional wicking layer may be disposed as an inner layer of inner conduit 20, configured to be in contact with breathing gas flow (B) inside said conduit. Such a wicking layer may be made of wicking material which allows for adsorption and/or absorption of both moisture and water in any phase, gas or liquid, using a capillary action, while the outer layer of water vapor breathable medium permits the passage of water vapor only and not liquid water.

Examples of wicking material in the inner layer are a knit or non-woven cloth or fabric, and can be synthetic and made of polyester, polyester and polypropylene blends, nylon, polyethylene or paper, and can be microfilaments or microfiber material such as Evolon® brand fabric material made by Freudenberg & Co. KG. A particular example of wicking material would be a non-woven material of 70% polypropylene and 30% polyester. Another example of the wicking material can be Evolon® brand fabric material having a weight of 60 or 80 grams per square meter. Examples of the outer layer of water vapor breathable medium are Sympatex® brand water vapor permeable membranes made of polymers made by Sympatex Technologies, including monolithic hydrophilic polyester ester membrane, including, as one example, a 12 micron thick membrane.

In another embodiment of the present invention, the breathing circuit tubing 11 comprises one or more small openings or perforations (not shown) in inner tube 20 which permit drainage of liquid water from the breathing gas conduit 12 to the dry gas conduit 14, such that another, different, moisture transmission pathway T1 is provided by such one or more perforations between the breathing gas flow (B) and dry gas flow (D), such as shown in FIG. 2.

Figure 3:
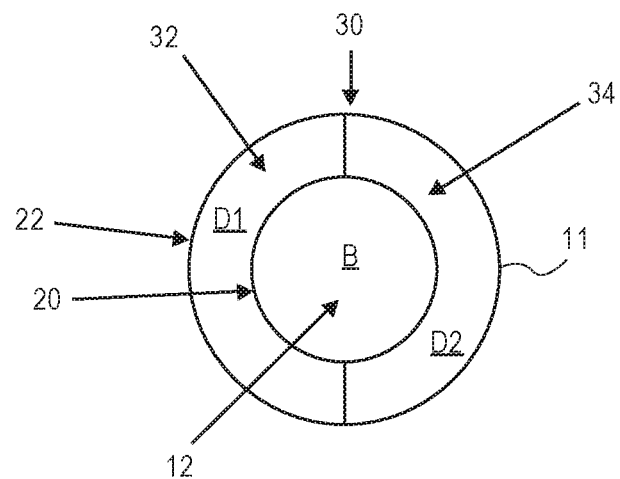
FIG. 3 a schematic cross-sectional view illustrating the apparatus of FIG. 1 in one or more additional embodiments of the present invention.

FIG. 3 a schematic cross-sectional view illustrating the apparatus of FIG. 1 in one or more additional embodiments of the present invention. In FIG. 3, a dividing wall 30 is formed between the inner tube 20 and outer tube 22 in the annular space between said tubes to divide the dry gas conduit into a first, delivery conduit 32 for flow of dry gas (D1) from a first end of the apparatus 10 to a second end of the apparatus, and a second, return conduit 34 for flow of dry gas (D2) from the second end of the apparatus to the first end of the apparatus 10. In this way, the dry gas flow may be re-used, such as, for example, in a closed loop system. One or more moisture transmission pathways may be defined between breathing gas flow conduit (B) and one or both of dry gas conduits (D1, D2), including a permeable membrane incorporated into inner tube 20 as described herein, or a series of perforations in the inner tube 20, as also described herein. The permeable membrane is permeable to water vapor but impermeable to liquid water and may include one or more layers, including a wicking layer, as described above.

Figure 4:
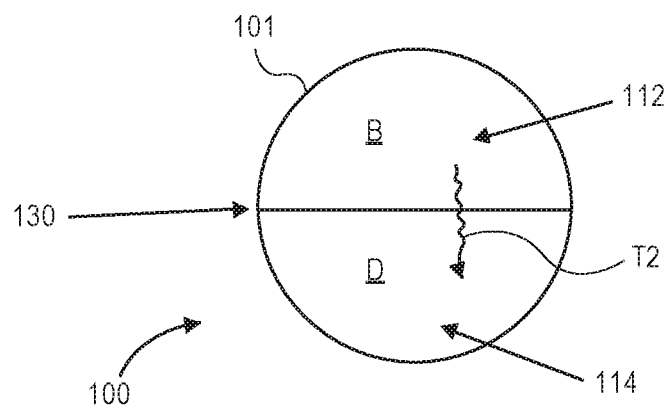
FIG. 4 is a schematic cross sectional view of an apparatus incorporated into or as part of a breathing gas circuit in accordance with one or more additional embodiments of the present invention.

FIG. 4 is a schematic cross sectional view of an apparatus 100 incorporated into or as part of a breathing gas circuit in accordance with one or more additional embodiments of the present invention. In FIG. 4, a breathing circuit tubing 101 defines a breathing gas conduit 112 for a flow of breathing gas flow (B) therein, said breathing gas having a first humidity level and a level of moisture therein, and a dry gas conduit 114 is formed adjacent at least a portion of the breathing gas conduit 112 for a dry gas flow (D) therein, said dry gas flow configured to have a second humidity level lower than the first humidity level. In FIG. 4, a moisture transmission pathway (T2) is provided between the breathing gas conduit 112 and the dry gas conduit 114, such that humidity in the flow of breathing gas (B) is lowered and moisture in the flow of breathing gas (B) is transferred to the dry gas flow (D). In FIG. 4, the breathing gas conduit 112 and dry gas conduit 114 share a common dividing wall 130, the common dividing wall 130 having the moisture transmission pathway (T2), which may be provided by a permeable membrane incorporated into part or all of the dividing wall 130, as described herein, or a series of perforations in part or all of the dividing wall 130, as also described herein. The permeable membrane is permeable to water vapor but impermeable to liquid water and may include one or more layers, including a wicking layer, as described above.

In one or more embodiments of the present invention, the dry gas conduit 14, 32, 34, 114 can be closed to ambient air around the apparatus. The dry gas conduit therefore can be configured to provide a stream of dry gas flow at humidity levels which are significantly lower than the humidity in the breathing gas conduit 12, 112. An exit port for the dry gas conduit may further include a filter, the dry gas exiting via the exit port to the ambient environment surrounding the apparatus. Such an exit port may also be connected to a source of suction. An input port for the dry gas conduit may include a flow or volumetric control element for the dry gas flow.

The present invention therefore uses the differential between humidity or moisture content between the respective flows in the breathing gas conduit 12, 112, vs. the dry gas conduit 14, 32, 34, 114, which allows for greater extraction or diffusion of moisture and humidity from the breathing gas flow to the dry gas flow, which is further assisted by the convective action of the dry gas flow along the common surface area shared between the breathing gas conduit 12, 112, and the dry gas conduit 14, 32, 34, 114, such as along inner conduit 20, or common dividing wall 130.

The present invention therefore provides a superior way of removal of moisture or water vapor from a breathing circuit, which is better than water traps or other fluid dissipation or moisture removal devices known in the prior art. The result of the inventive apparatus disclosed is that when the apparatus is coupled with a breathing circuit, rainout or condensation in the breathing tube and collection of water within the breathing circuit is significantly reduced. The present invention therefore allows for removal of the collected condensate on the inner walls of a breathing gas conduit, which is then transported away through an outer sleeve which provides the dry gas conduit. The outer tube of the apparatus can also serve to protect the inner tube from damage or puncture, which can be especially vulnerable to damage or puncture when it incorporates a permeable membrane and/or perforations as described herein. To provide additional strength and puncture protection, an additional outer cover structure can be added to the apparatus. The present invention therefore represents an improvement over the known prior art by providing the benefits of: (a) reducing or eliminating user management of condensate levels within a breathing circuit, and/or (b) reducing the humidity output from an expiratory limb of a breathing circuit to reduce the collection of condensate which may be collected in the ventilator.

The many features and advantages of the invention are apparent from the detailed specification, and thus, it is intended by the appended claims to cover all such features and advantages of the invention which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

The invention claimed is:

1. A moisture removal and condensation and humidity management apparatus incorporated into a breathing circuit arranged between a patient and a ventilator, comprising:
   a breathing circuit tubing formed by an inner tube and defining a breathing gas conduit between the patient and the ventilator for a flow of breathing gas therein, said breathing gas having a first humidity level and a level of moisture or condensate therein, and
   a dry gas conduit formed by an outer tube surrounding the inner tube, an annular space being defined between the inner tube and the outer tube, the dry gas conduit adjacent at least a portion of the breathing gas conduit for a dry gas flow in said dry gas conduit, said dry gas flow configured to have a second humidity level lower than the first humidity level,
   a moisture transmission pathway between the breathing gas conduit and the dry gas conduit, such that humidity in the flow of breathing gas is lowered and moisture in the flow of breathing gas is transferred to the dry gas flow, and
   a dividing wall formed between the inner tube and outer tube in the annular space to divide the dry gas conduit into a first, delivery conduit for flow of dry gas from a first end of the apparatus to a second end of the apparatus, and a second, return conduit for flow of dry gas from the second end of the apparatus to the first end of the apparatus,
   wherein the dry gas flow is coupled from a dry gas source to one or more input ports which feed the dry gas flow into the dry gas conduit,
   wherein the dry gas flow exits via an exit port to the ambient environment surrounding the apparatus,
   wherein the breathing circuit tubing forming the breathing gas conduit between the patient and the ventilator comprises a permeable portion which is permeable to water vapor but impermeable to liquid water, such that the moisture transmission pathway is provided by the permeable portion of the breathing circuit tubing,
   wherein the breathing circuit tubing comprising said permeable portion and said dry gas conduit is an expiratory limb of said breathing circuit disposed between the patient and the ventilator, and wherein said expiratory limb comprising said permeable portion of the breathing circuit tubing is downstream of the patient and upstream of the ventilator, and
   wherein the permeable portion is a permeable membrane which forms the walls of the inner tube forming the breathing gas conduit.

2. The apparatus of claim 1, wherein the breathing circuit tubing comprises one or more perforations which permit drainage of liquid water from the breathing gas conduit to the dry gas conduit, such that the moisture transmission pathway is further provided by such one or more perforations of the breathing circuit tubing.

3. The apparatus of claim 1, wherein the dividing wall comprises the permeable portion which is permeable to water vapor but impermeable to liquid water, such that the moisture transmission pathway is provided by such permeable portion of the dividing wall.

4. The apparatus of claim 3, wherein the permeable portion of the breathing circuit tubing is the permeable membrane which forms a portion of said dividing wall.

5. The apparatus of claim 1, wherein the dividing wall comprises one or more perforations which permit drainage of liquid water from the breathing gas conduit to the dry gas conduit, such that the moisture transmission pathway is further provided by such one or more perforations of the dividing wall.

6. The apparatus of claim 1, wherein the exit port for the dry gas conduit comprises a filter.

7. The apparatus of claim 1, further comprising:
   a flow or volumetric control element for the dry gas flow.

8. A method of removing moisture or controlling condensation in a breathing circuit, comprising:
   providing a moisture removal and condensation and humidity management apparatus incorporated into a breathing circuit arranged between a patient and a ventilator, comprising a breathing circuit tubing formed by an inner tube and defining a breathing gas conduit between the patient and the ventilator for a flow of breathing gas therein, said breathing gas having a first humidity level and a level of moisture or condensate therein, a dry gas conduit formed by an outer tube surrounding the inner tube, an annular space being defined between the inner tube and the outer tube, the dry gas conduit adjacent at least a portion of the breathing gas conduit for a dry gas flow in said dry gas conduit, said dry gas flow configured to have a second humidity level lower than the first humidity level, a moisture transmission pathway between the breathing gas conduit and the dry gas conduit, such that humidity in the flow of breathing gas is lowered and moisture in the flow of breathing gas is transferred to the dry gas flow, and a dividing wall formed between the inner tube and outer tube in the annular space to divide the dry gas conduit into a first, delivery conduit for flow of dry gas from a first end of the apparatus to a second end of the apparatus, and a second, return conduit for flow of dry gas from the second end of the apparatus to the first end of the apparatus, wherein the breathing circuit tubing forming the breathing gas conduit between the patient and the ventilator comprises a permeable portion which is permeable to water vapor but impermeable to liquid water, such that the moisture transmission pathway is provided by the permeable portion of the breathing circuit tubing;

wherein the breathing circuit tubing comprising said permeable portion and said dry gas conduit is an expiratory limb of said breathing circuit disposed between the patient and the ventilator, and wherein said expiratory limb comprising said permeable portion of the breathing circuit tubing is downstream of the patient and upstream of the ventilator;

wherein the permeable portion is a permeable membrane which forms the walls of the inner tube forming the breathing gas conduit;

wherein the dry gas flow is coupled from a dry gas source to one or more input ports which feed the dry gas flow into the dry gas conduit, wherein the dry gas flow exits via an exit port to the ambient environment surrounding the apparatus;

said method further comprising:

supplying or receiving breathing gas via the breathing circuit tubing to or from a patient, and supplying dry air through the dry gas conduit to remove moisture or liquid water condensate from the breathing gas conduit.

9. The method of claim 8, further comprising:

monitoring one or more of the first and second humidity levels using a humidity sensor.

10. A moisture removal and condensation and humidity management apparatus incorporated into a breathing circuit arranged between a patient and a ventilator, comprising:

a breathing circuit tubing formed by an inner tube and defining a breathing gas conduit between the patient and the ventilator for a flow of breathing gas therein, said breathing gas having a first humidity level and a level of moisture or condensate therein, and a dry gas conduit formed by an outer tube surrounding the inner tube, an annular space being defined between the inner tube and the outer tube, the dry gas conduit adjacent at least a portion of the breathing gas conduit for a dry gas flow in said dry gas conduit, said dry gas flow configured to have a second humidity level lower than the first humidity level, a moisture transmission pathway between the breathing gas conduit and the dry gas conduit, such that humidity in the flow of breathing gas is lowered and moisture in the flow of breathing gas is transferred to the dry gas flow, and a dividing wall formed between the inner tube and outer tube in the annular space to divide the dry gas conduit into a first, delivery conduit for flow of dry gas from a first end of the apparatus to a second end of the apparatus, and a second, return conduit for flow of dry gas from the second end of the apparatus to the first end of the apparatus, wherein the breathing circuit tubing comprises one or more perforations which permit drainage of liquid water from the breathing gas conduit to the dry gas conduit, such that the moisture transmission pathway is further provided by such one or more perforations of the breathing circuit tubing, wherein the dry gas flow is coupled from a dry gas source to one or more input ports which feed the dry gas flow into the dry gas conduit, wherein the dry gas flow exits via an exit port to the ambient environment surrounding the apparatus, wherein the breathing circuit tubing forming the breathing gas conduit between the patient and the ventilator comprises a permeable portion which is permeable to water vapor but impermeable to liquid water, such that the moisture transmission pathway is provided by the permeable portion of the breathing circuit tubing, wherein the breathing circuit tubing comprising said permeable portion and said dry gas conduit is an expiratory limb of said breathing circuit disposed between the patient and the ventilator, and wherein said expiratory limb comprising said permeable portion of the breathing circuit tubing is downstream of the patient and upstream of the ventilator, and wherein the permeable portion is a permeable membrane which forms the walls of the inner tube forming the breathing gas conduit.

* * * * *